(12) United States Patent
Tartaglione et al.

(10) Patent No.: US 12,011,344 B1
(45) Date of Patent: Jun. 18, 2024

(54) DROOL GUARD

(71) Applicants: Michael A. Tartaglione, Naples, FL (US); Sandra J. Tartaglione, Naples, FL (US)

(72) Inventors: Michael A. Tartaglione, Naples, FL (US); Sandra J. Tartaglione, Naples, FL (US)

( * ) Notice: Subject to any disclaimer, the term of this patent is extended or adjusted under 35 U.S.C. 154(b) by 0 days.

(21) Appl. No.: 18/108,710

(22) Filed: Feb. 13, 2023

(51) Int. Cl.
| | |
|---|---|
| *A61B 5/097* | (2006.01) |
| *A61B 5/00* | (2006.01) |
| *A61F 5/56* | (2006.01) |
| *A61F 13/20* | (2006.01) |
| *A61L 31/04* | (2006.01) |
| *A61M 31/00* | (2006.01) |
| *A61J 11/00* | (2006.01) |
| *A61J 17/00* | (2006.01) |

(52) U.S. Cl.
CPC ...... *A61F 13/2008* (2013.01); *A61F 13/2022* (2013.01); *A61J 11/0075* (2013.01); *A61J 17/10* (2020.05)

(58) Field of Classification Search
CPC .. A61F 13/20; A61F 13/2008; A61F 13/2022; A63B 71/085; A63B 2071/088; A63B 2071/086
See application file for complete search history.

(56) References Cited

U.S. PATENT DOCUMENTS

| | | | |
|---|---|---|---|
| 3,339,547 A | 9/1967 | Drabkowski | |
| 8,122,890 B2 | 2/2012 | Vaska | |
| 8,505,541 B2 | 8/2013 | Bardach et al. | |
| 8,745,802 B2 | 6/2014 | Steur | |
| 9,308,064 B2 | 4/2016 | Binner et al. | |
| 9,770,643 B2 | 9/2017 | Hawkins | |
| 10,595,759 B2 | 3/2020 | Wang et al. | |
| 2010/0004555 A1 * | 1/2010 | Bazemore | A61B 10/0051 600/573 |
| 2014/0238417 A1 * | 8/2014 | Turkbas | A61C 19/063 128/861 |
| 2016/0230007 A1 * | 8/2016 | Johnson | C08L 91/06 |
| 2022/0117801 A1 * | 4/2022 | Strane | A61F 13/2068 |

* cited by examiner

*Primary Examiner* — Todd J Scherbel
(74) *Attorney, Agent, or Firm* — Bryan L. Loeffler, Esq.; LOEFFLER IP GROUP, P.A.

(57) ABSTRACT

A drool guard (1) that is worn in the mouth to capture excess saliva and prevent drool from escaping a user's mouth while sleeping and when in public.

3 Claims, 4 Drawing Sheets

DROOL GUARD

FIELD OF THE INVENTION

This invention generally relates to drooling caused by the production of excess saliva, and more particularly, to a drool guard that is worn in the mouth and that captures excess saliva, thereby preventing drool from escaping the user's mouth.

BACKGROUND OF THE INVENTION

Drooling is characterized by saliva unintentionally and/or involuntarily flowing out of an individual's mouth. This is primarily caused by the production of excess saliva due to excess production of saliva.

For example, drooling in infants and toddlers is normal and may be associated with teething. Likewise, most drooling in teenagers and adults is just a common inconvenience that occurs while sleeping and resulting in ruined pillows and bedding.

In more serious cases, drooling is associated with cerebral palsy and other neurodegenerative disorders, wherein drooling in public situations can cause social stigmatization and emotional distress for the afflicted individuals and their families.

Therefore, a need exists for a drool guard that captures excess saliva and prevents drool from escaping the user's mouth.

SUMMARY OF THE INVENTION

The primary object of the present invention is to provide a drool guard that is worn in the mouth and that captures excess saliva, thereby preventing drool from escaping the user's mouth.

An additional object of the present invention is to provide a drool guard that may be safely worn while sleeping.

The present invention achieves the above and other objects by providing a drool guard that anchors within a user's mouth. A preferred embodiment of the present invention includes a substantially C-shaped semi-rigid flexible tray that fits over a user's upper and/or lower teeth. An outer surface of the tray has an absorbent surface capable of capturing and trapping saliva. The absorbent surface area may have an absorbent structure, such as gauze, sponge, cotton, paper, and so forth, that absorbs and retains excess saliva. The absorbent structure of the absorbent surface area may further have a distribution component, such as grooves or channels, that spread collected saliva across the absorbent surface for increased probability of absorption and retention of the saliva. In addition, the absorbent surface material may have a fluid acquisition layer to keep the top surface thereof dry to prevent clinging of the absorbent surface to the inside of the mouth and/or teeth. The fluid acquisition layer is preferably a porous outer surface, such as a perforated film. Alternatively, the entire tray may be constructed from the absorbent structure and then covered in a distribution component and/or fluid acquisition layer if so desired.

The tray may be C-shaped to fit over a user's side and front teeth as described above or the tray may have a straight body section that fits over the user's upper and/or lower molars and rear teeth where excess saliva normally pools between the check and gums.

Alternatively, the body of the drool guard may be shaped like a nipple of a conventional pacifier that also has a shield and a handle attached thereto. The shield may further have an absorbent layer covering an inner surface thereof to capture any drool that may escape a baby's or toddler's mouth.

Other features of the present invention include impregnating the mouth guard and absorbent surface area thereof with flavorings and other compounds that prevent bad morning breath and/or control bacteria in a user's mouth.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
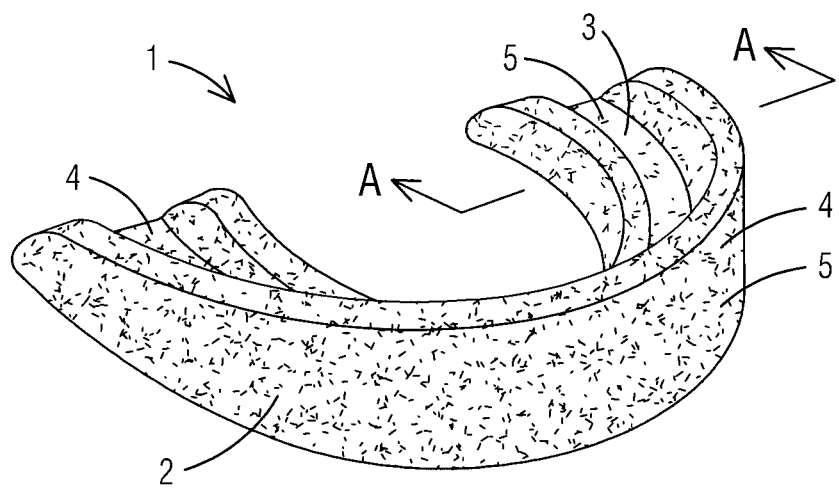
FIG. 1 is a perspective top view of a drool guard of the present invention having a body defined by a U-shaped tray.
Figure 2:
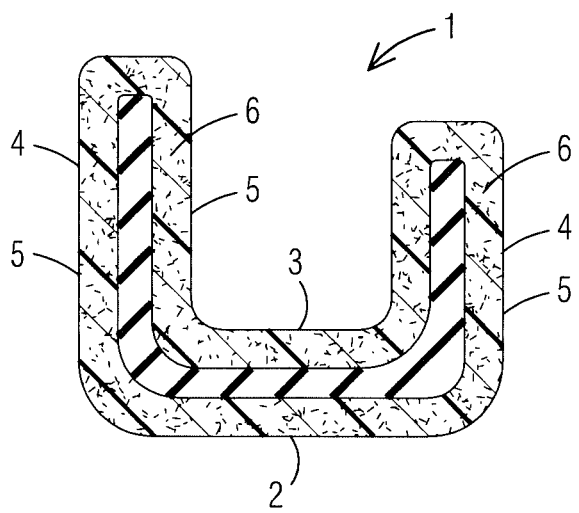
FIG. 2 is a sectional view along lines A-A of FIG. 1.
Figure 3:
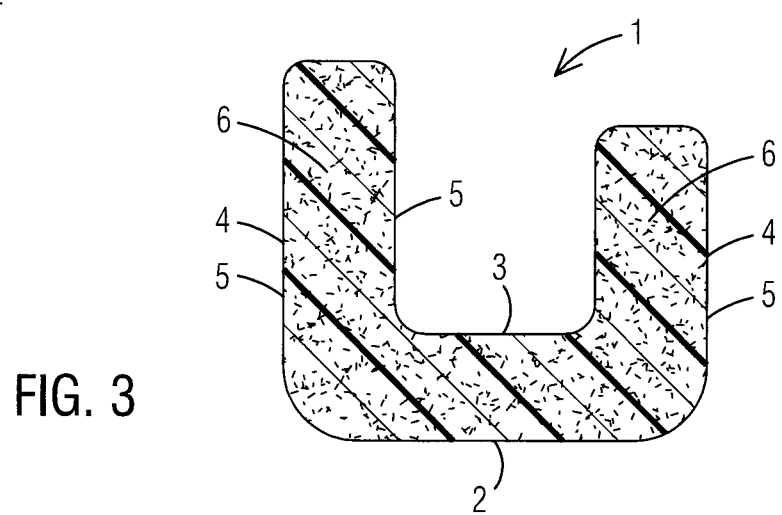
FIG. 3 is a sectional view along lines A-A of FIG. 1.
Figure 11:
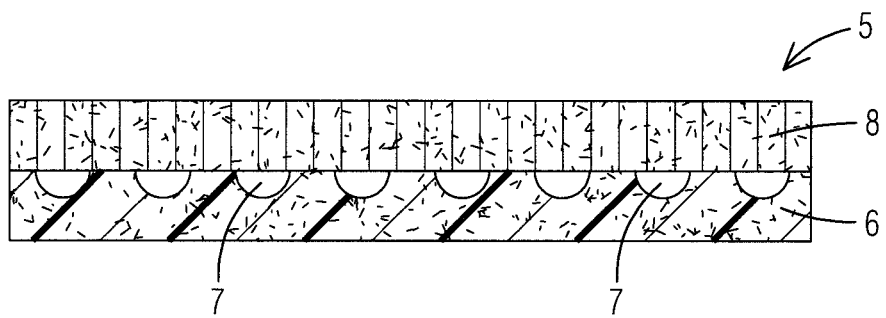
FIG. 11 is and exemplary cross-sectional view of an absorbent surface area of the present invention.

For purposes of describing the preferred embodiment, the terminology used in reference to the numbered accessories in the drawings is as follows:

1. drool guard, generally
2. body
3. tray
4. outer surface of body
5. absorbent surface area
6. absorbent structure
7. distribution component
8. fluid acquisition layer
9. pacifier nipple
10. shield
11. handle
12. bottle nipple
13. nipple ring
14. bottle With reference to FIGS. 1-3, a drool guard 1 of the present invention if illustrated wherein the drool guard 1 comprises a body 2 defined by a C-shaped semi-rigid flexible tray 3 having a substantially U-shaped or J-shaped profile that fits over a user's upper and/or lower teeth. An outer surface 4 of the body 2 has at least one absorbent surface area 5 capable of capturing and trapping saliva. The absorbent surface area 5 is made up of an absorbent structure 6, such as gauze, sponge, cotton, paper, and so forth, capable of absorbing and retaining excess saliva. The absorbent surface area 5 may further comprise a distribution component 7, such as grooves or channels, that spread collected saliva across the absorbent structure 6 for increased probability of absorption and retention of saliva. In addition, the absorbent surface area 5 may further comprise a fluid acquisition layer 8 to keep the top surface of the absorbent structure 6 dry, thereby prevent clinging of the absorbent surface to the inside of the mouth and/or user's teeth. The fluid acquisition layer 8 is preferably a porous layer of material, such as a perforated film, as further illustrated in FIG. 11.

The tray 3 may be partially constructed from a flexible semi-rigid material, such as rubber or plastic, as illustrated in FIG. 2. Alternatively, the tray 3 may be constructed entirely out of the absorbent structure 6, such as sponge, and then covered in a distribution component 7 and/or fluid acquisition layer of desired 8 as illustrated in FIG. 3.

Figure 4:
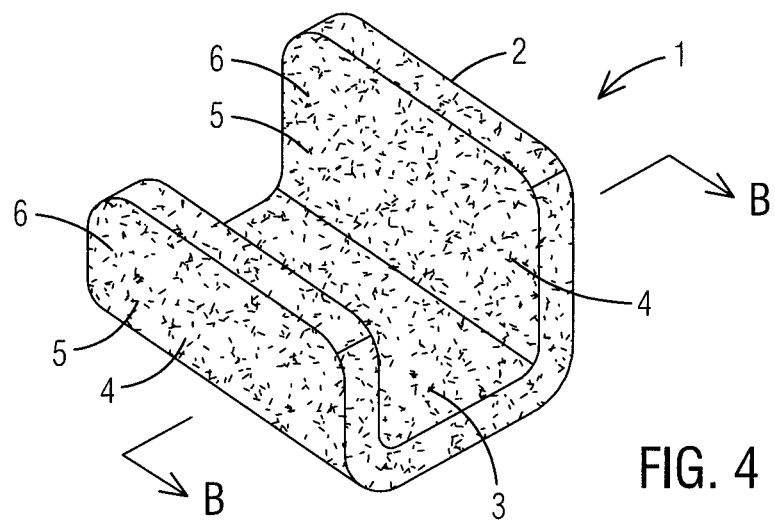
FIG. 4 is a perspective top view of a drool guard of the present invention having a body defined by straight section of tray.
Figure 5:
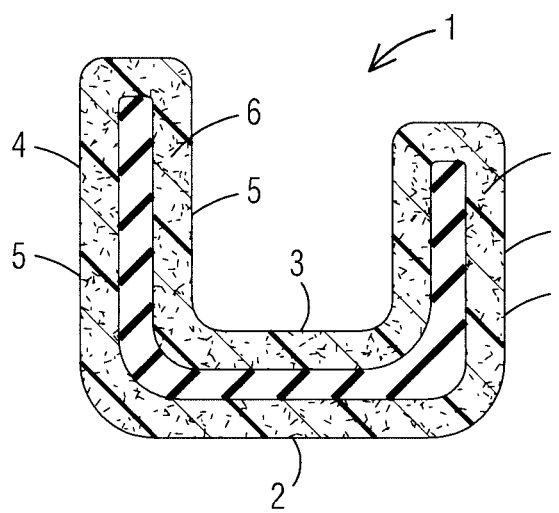
FIG. 5 is a sectional view along lines B-B of FIG. 4.
Figure 6:
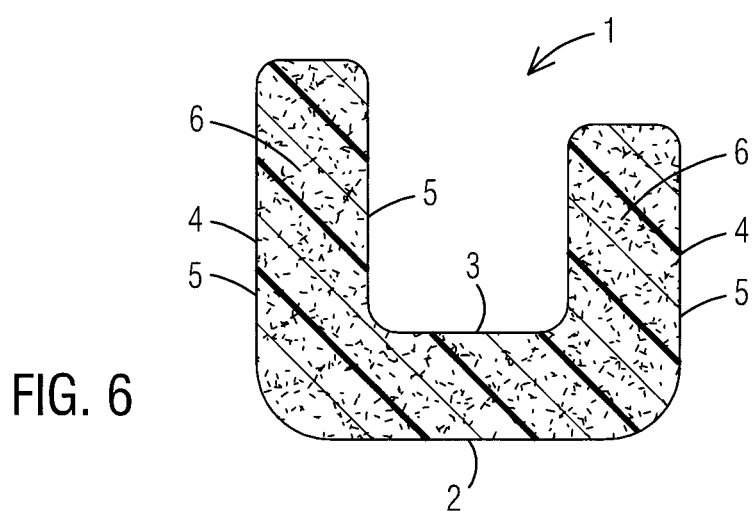
FIG. 6 is a sectional view along lines B-B of FIG. 4.
Figure 7:
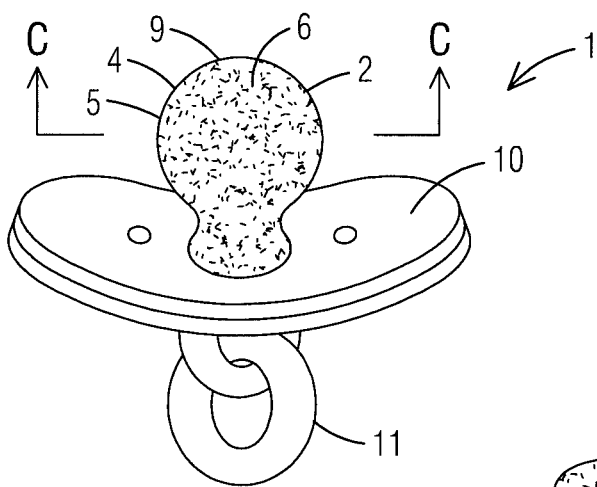
FIG. 7 is a perspective top view of a drool guard of the present invention having a body defined by round pacifier nipple.
Figure 8:
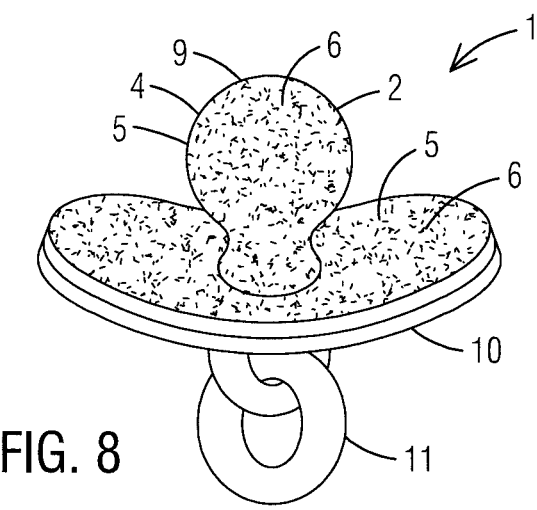
FIG. 8 is a perspective top view of a drool guard of the present invention having a body defined by round pacifier nipple and having an absorbent surface area on a shield thereof.

With reference to FIGS. 4-6, a drool guard 1 of the present invention is illustrated in which the body 2 is a straight section of tray 3 having a substantially U-shaped and J-shaped profile that fits over a user's upper and/or lower molars and rear teeth where excess saliva normally pools between the check and gums. An outer surface 4 of the tray 3 has at least one absorbent surface area 5 capable of capturing and trapping saliva. The absorbent surface area 5 may further comprise a distribution component 7, such as grooves or channels, that spread collected saliva across the absorbent structure 6 for increased probability of absorption and retention of saliva. In addition, the absorbent surface area 5 may further comprise a fluid acquisition layer 8 to keep the top surface of the absorbent structure 6 dry, thereby prevent clinging of the absorbent surface to the inside of the mouth and/or user's teeth. The fluid acquisition layer 8 is preferably a porous layer of material, such as a perforated film, as further illustrated in FIG. 11.

The tray 3 may be partially constructed from a flexible semi-rigid material, such as rubber or plastic, as illustrated in FIG. 5. Alternatively, the tray 3 may be constructed entirely out of the absorbent structure 6, such as sponge, and then covered in a distribution component 7 and/or fluid acquisition layer of desired 8 as illustrated in FIG. 6.

With reference to FIGS. 7-11, a drool guard 1 of the present invention is illustrated in which the body 2 forms a round pacifier nipple 9 attached to a shield 10 and a handle 11. An outer surface 4 of the nipple has at least one absorbent surface area 5 capable of capturing and trapping saliva. The absorbent surface area 5 may further comprise a distribution component 7, such as grooves or channels, that spread collected saliva across the absorbent structure 6 for increased probability of absorption and retention of saliva. In addition, the absorbent surface area 5 may further comprise a fluid acquisition layer 8 to keep the top surface of the absorbent structure 6 dry, thereby prevent clinging of the absorbent surface to the inside of the mouth and/or user's teeth. The fluid acquisition layer 8 is preferably a porous layer of material, such as a perforated film, as further illustrated in FIG. 11.

Figure 10:
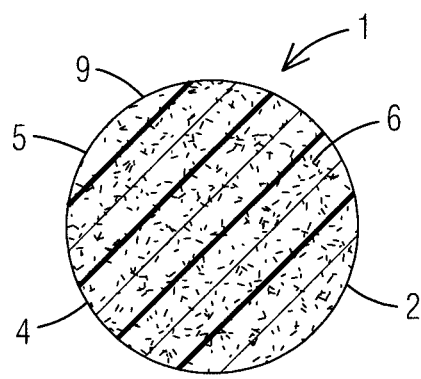
FIG. 10 is a sectional view along lines C-C of FIG. 7.
Figure 9:
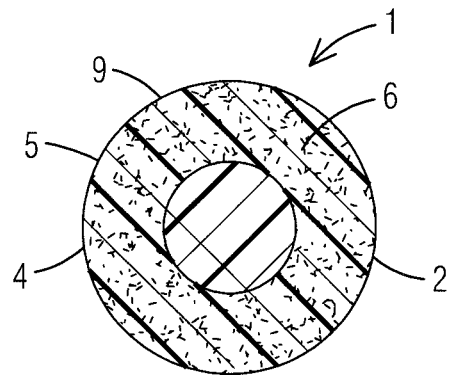
FIG. 9 is a sectional view along lines C-C of FIG. 7.

The pacifier nipple 9 may be partially constructed from a flexible semi-rigid material, such as rubber or plastic, as illustrated in FIG. 9. Alternatively, the pacifier nipple 9 may be constructed entirely out of the absorbent structure 6, such as sponge, and then covered in a distribution component 7 and/or fluid acquisition layer of desired 8 as illustrated in FIG. 10. The present invention may also be used in medical and dental offices with patients who have undergone dental or oral surgeries, post-surgery for the absorption of blood and other fluids.

Other features of the present invention include impregnating the mouth guard 1 and absorbent surface area 5 thereof with flavorings and other oral-care compounds that prevent bad morning breath and/or control bacteria in a user's mouth.

Figure 12:
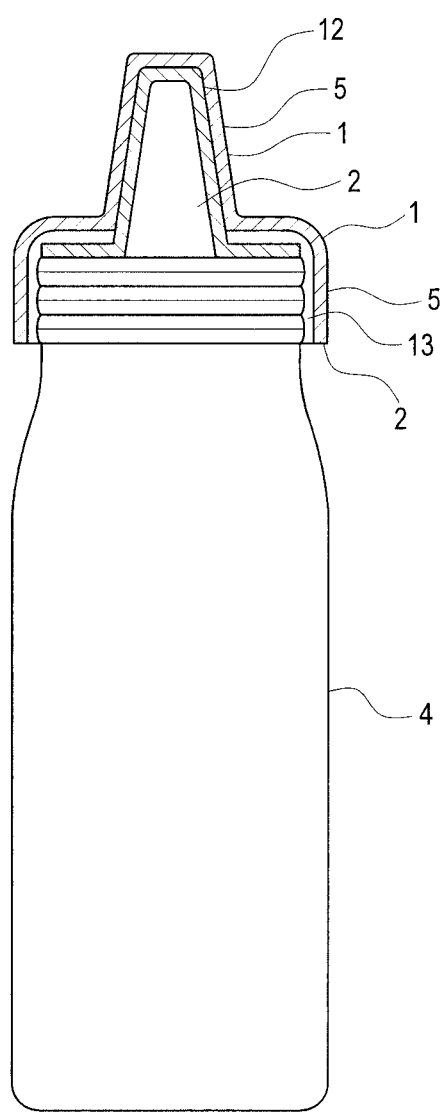
FIG. 12 is a partial cutaway side view of a drool guard of the present invention having a body defined by bottle nipple and a pacifier ring.

With reference to FIG. 12, a partial cutaway side view of a drool guard 1 of the present invention having a body 2 defined by a bottle nipple 12 and a nipple ring 13 is illustrated. Additional embodiments of the present invention include a screw on nipple ring 13 and bottle nipple 12 for bottles 14, such as baby bottle and sippy cups wherein the bottle nipple 12 and is secured to the bottle 14 using a threaded nipple ring 13. An outer surface of the threaded ring preferably comprises at least one absorbent surface area 5 capable of capturing and trapping any drool, milk, formula, juice, etc. that may escape a baby's or toddler's mouth while drinking from the bottle nipple 12, thereby reducing rashes and eczema outbreaks commonly caused by excess moisture around a baby's mouth. In addition, the reduction of drool within the mouth reduces the likelihood that an individual or baby's gag reflex will be irritated, thereby reducing coughing, spitting up, and vomiting that can be caused when excess drool and/or other fluids collect in the mouth.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, We claim:

1. A drool guard comprising:
    a semi-rigid flexible body defined by a C-shaped flexible tray having a substantially U-shaped profile capable of fitting over a user's upper and/or lower teeth;
    wherein said U-shaped profile fully extends around the C-shaped flexible tray; said body having an outer surface with at least one absorbent structure located thereon;
    said at least one absorbent structure having an absorbent surface area capable of capturing and trapping saliva; and
    a fluid acquisition layer covering the absorbent surface area which allows saliva to pass through to the absorbent surface area to be absorbed while keeping the top surface of the absorbent structure dry to prevent sticking to a user's teeth or gums.

2. The drool guard of claim 1 wherein:
    said fluid acquisition layer is a perforated film.

3. The drool guard of claim 1 wherein:
    said body defined by a the having a substantially J-shaped profile capable of fitting over a user's upper and/or lower teeth; and
    wherein said J-shaped profile fully extends around the C-shaped flexible tray.

* * * * *